United States Patent [19]

Ross

[11] 4,069,420
[45] Jan. 17, 1978

[54] OPTICAL GAS ANALYZER

[75] Inventor: Thaddeus C. Ross, Santa Barbara, Calif.

[73] Assignee: Cavitron Corporation, New York, N.Y.

[21] Appl. No.: 664,464

[22] Filed: Mar. 8, 1976

[51] Int. Cl.$^2$ ............................................. G01N 21/26
[52] U.S. Cl. ..................................... 250/341; 250/343
[58] Field of Search ............... 250/340, 341, 343, 344, 250/345, 346, 373

[56] References Cited

U.S. PATENT DOCUMENTS

| | | | |
|---|---|---|---|
| 3,171,027 | 2/1965 | Wallack | 250/343 |
| 3,206,597 | 9/1965 | Fertig | 250/343 |
| 3,562,524 | 2/1971 | Moore | 250/343 |
| 3,700,891 | 10/1972 | Friedrich | 250/343 |
| 3,709,600 | 1/1973 | Ganshorn | 250/343 |
| 3,911,277 | 10/1975 | Cederstrand | 250/343 |
| 3,932,754 | 1/1976 | Riedl | 250/343 |
| 3,976,883 | 8/1976 | Krakow | 250/343 |

Primary Examiner—Craig E. Church
Attorney, Agent, or Firm—Philip Sperber

[57] ABSTRACT

An optical gas analyzer is disclosed utilizing the infrared absorption principle having a sample chamber and reference chamber with infrared source and detector assembly spaced at opposite ends of and in alignment with the chambers with baffle means provided in cooperating relation with the infrared source to prevent cross-currents with respect thereto and masking means provided in cooperating relation with the detector assembly to mask out a gas having a partially overlapping infrared absorption band. The electronic processing system utilizes the total area under the signal waveform to derive the desired measurement. In addition barometric correction means is provided to permit on site calibration by the user of the gas analyzer.

44 Claims, 15 Drawing Figures

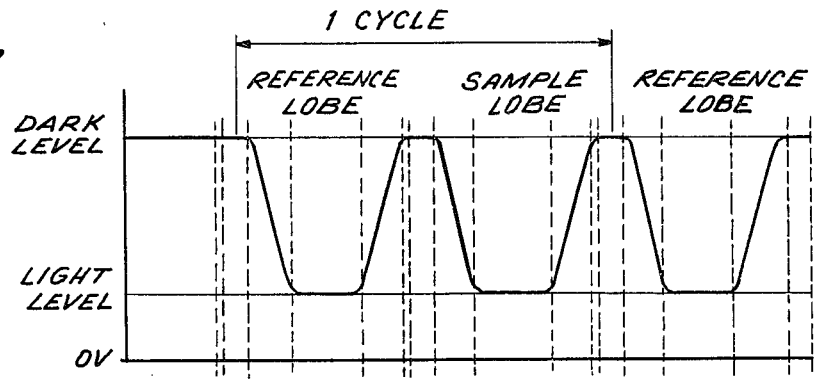
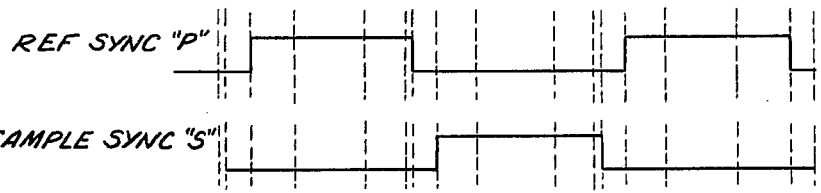
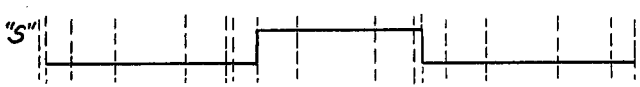
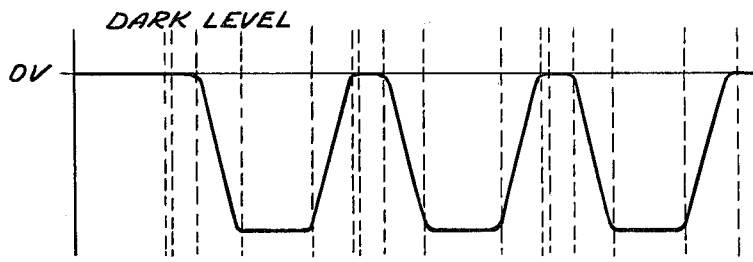
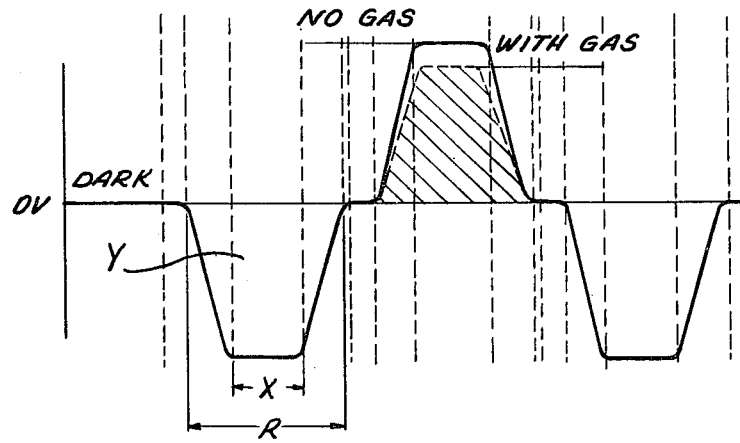
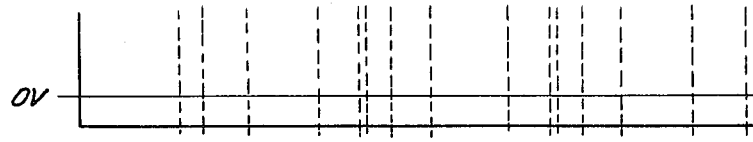

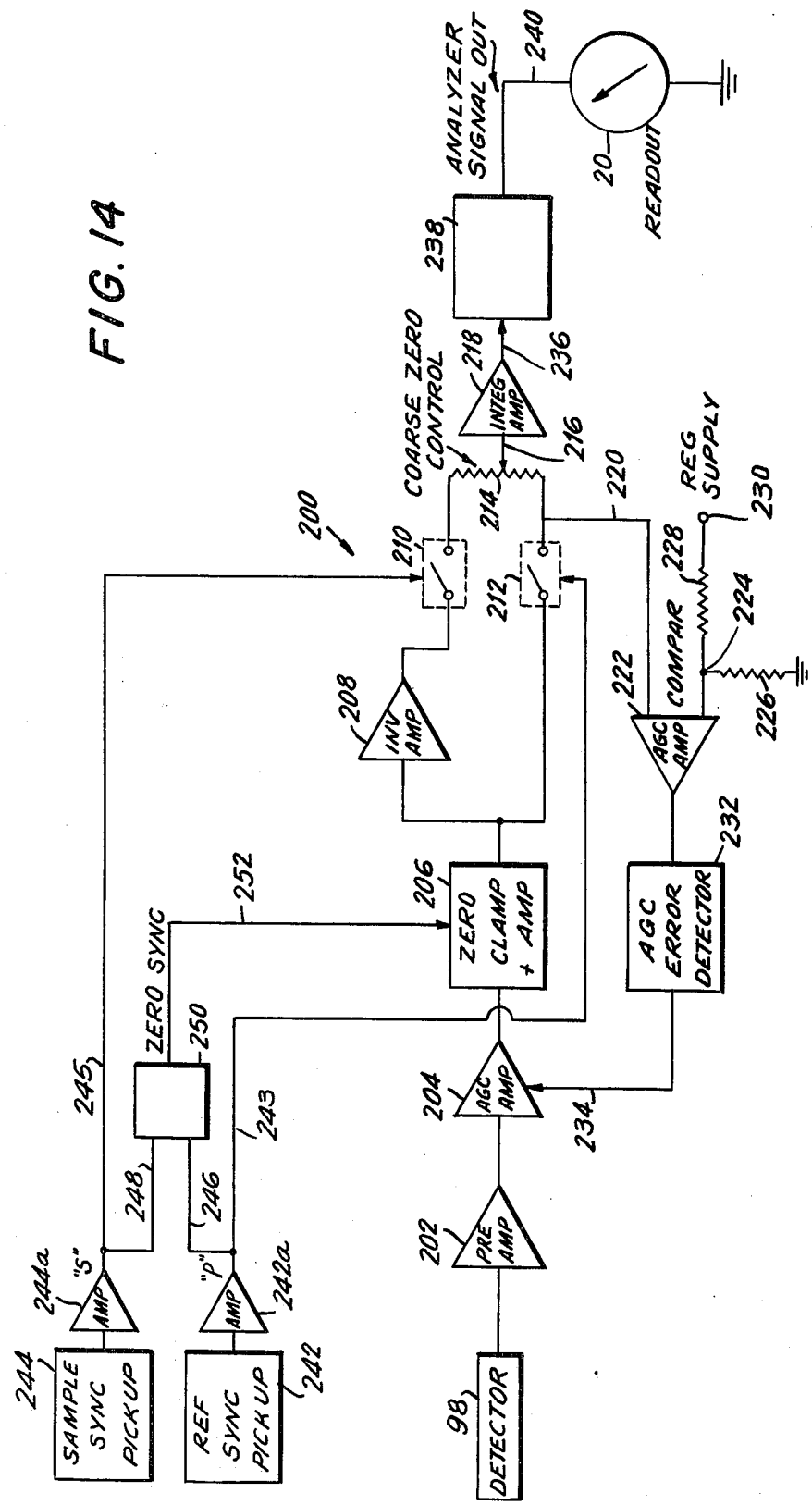

OPTICAL GAS ANALYZER

BACKGROUND OF INVENTION

1. Field of the Invention

The present invention relates to improvement in optical gas analyzers and more particularly, to refinements in non-dispersive infrared analyzers in order to obtain adequate performance for medical and other precision applications.

2. Description of Prior Art

The inventor of the present invention has contributed to the prior art devices in the area of infrared gas analyzers and this prior art as exemplified in U.S. Pat. No. 3,932,754 substantially sets forth one aspect of devices commercially utilized to date for non-medical applications. The inventor in setting forth to perfect instrumentation for medical applications found that the prior art teachings contained in the above referenced patent and others known in the art, lacked the degree of reliability and sophistication necessary for medical applications.

Towards this end, when dealing with instrumentation in life support systems in which the output of information is of a critical nature the degree of calibration and other performance standards, as hereinafter explained in detail, was not available with the prior art equipment. Accordingly, although the present invention will be particularly discussed with respect to the benefits it provides for medical application, these same advantages also lend themselves to industrial and other applications as well.

OBJECTS OF THE INVENTION

An object of the present invention is to provide a non-dispersive infrared gas analyzer ideally suited for medical and other applications.

Another object of the present invention is the provision of a non-dispersive infrared gas analyzer having barometric compensation which corrects for variation in ambient barometric pressure by providing the user with a control which can be set accordingly to the barometric pressure existing at the moment.

Another object of the invention is to provide for non-dispersive infrared gas analyzer in which interferring gases can be masked out from the output by means of providing in association with the detector housing a backfill of the gas which is expected to be contained in the analysis stream but which it is desired to exclude from the analysis process even though its spectral absorption lines encroach in the spectrum of the gases of interest which are to be measured.

Another object of the invention is to provide means for quieting the output of the infrared emitter to keep the noise of the system to a minimum value.

Another object of the non-dispersive infrared gas analyzer invention is to provide an electronic processing system which will extract the maximum amount of information from the signal developed by the infrared detector to maximize the overall signal to noise ratio.

Other objects of the gas analyzer and advantages of the present invention will become obvious as the disclosure proceeds.

SUMMARY OF THE INVENTION

The non-dispersive analyzer of the present invention has been designed for use in medical gas applications. The gas analyzer measures the composition of inspired and expired gas to aid in monitoring of pulmonary and cardiovascular parameters in clinical and research applications. Carbon dioxide, nitrous oxide and selected Halogenated hydrocarbons are measured on a simultaneous and essentially instantaneous breath to breath basis.

Combined observation of respiratory gas composition, inhaled natural or substitute mixtures, in addition to flow, for example, lead to a number of useful metabolic and respiratory evaluations that are otherwise unavailable. This of course requires a reliable high sensitivity analyzer which does not exhibit cross-talk with interferring gases. The analyzer of the present invention compares the optical (infrared) transmittance of two identical optical paths. One optical path passes through the sample cell or chamber of unknown gas concentration, the other optical path passes through the reference cell or chamber. The difference in optical transmittance between these paths then is a measure of the optical absorption. The variation in transmittance is sensed by a photon detector and the signal from the detector is processed and used to drive the output as a direct measure of the concentration of the unknown gas.

The radiant beams, after passing through the sample and reference chamber are reflected and imaged by a mirror into a photon detector after first passing through the optical filter. The optical filter represents the precise "windows" of the absorption bands for the specific gases of interest.

In effect, then, the system is tuned to see only energy in those unique absorption bands which represent the gas of interest. Energy outside these bands whether as part of the chopped energy or stray "light" from other sources is eliminated. This stray energy could result in adding an undesirable level of noise or unwanted signal to the system if that energy were permitted to strike the detectors. The filters in essence block out all unwanted radiant energy.

In operation then, the system turned on and warmed up, sample gas (unknown) is introduced into the sample chamber. The alternating beam of radiant energy is directed first through the reference chamber and then to the sample chamber in a continual half-cycle interruption at the rate of 160 cycles per second. As the beam passes through the reference chamber, the energy of the beam is unattenuated and provides a standard of measurement. On the second half-cycle, as the beam passes through the sample chamber, the beam will be selectively attenuated by the gas of interest. If the gas is present in the sample chamber, the beam energy will be attenuated proportional to the gas concentration within the spectral bands and the signal will be modulated in proportion to the gas concentration.

In this way, the detector generates two electrical signals per chopper cycle—one representing reference level, the other the sample gas level. These signals are amplified, demodulated and then linearized for display on readout means that may be visual or on a recorder. Baffle means has been provided in cooperating relation with the infrared source to prevent cross-currents with respect thereto and masking means provided in cooperating relation with the detector assembly to mask out a gas having a partially overlapping infrared absorption band. The electronic processing system of the present invention utilizes the total area under the signal waveform to derive the desired measurement. In addition barometric correction means is provided to permit on site calibration by the user of the gas analyzer to eliminate the otherwise inevitable errors in readings of about 3% per inch of mercury ambient pressure change which normally result from gas expansion and contraction.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 7 illustrates the composite signal waveform out of the detector showing the dark levels and light levels;

FIG. 8 illustrates the waveform of the reference sync pulse;

FIG. 9 illustrates the waveform of the sample sync pulse;

FIG. 10 illustrates the waveform of the zero sync pulse;

FIG. 11 illustrates the waveform of the composite sample and reference signals relative to the ground level after zero clamping;

FIG. 12 illustrates a new composite waveform after inversion and multiplexing;

FIG. 13 illustrates the integrated level of voltage above ground of the waveform illustrated in FIG. 12;

FIG. 14 is a diagram generally illustrating the circuit means of the gas analyzer as it relates to the waveforms illustrated on FIGS. 7-13 for extracting the desired information from the detector signal for display by the readout.

DESCRIPTION OF THE PREFERRED EMBODIMENTS

Figure 1:
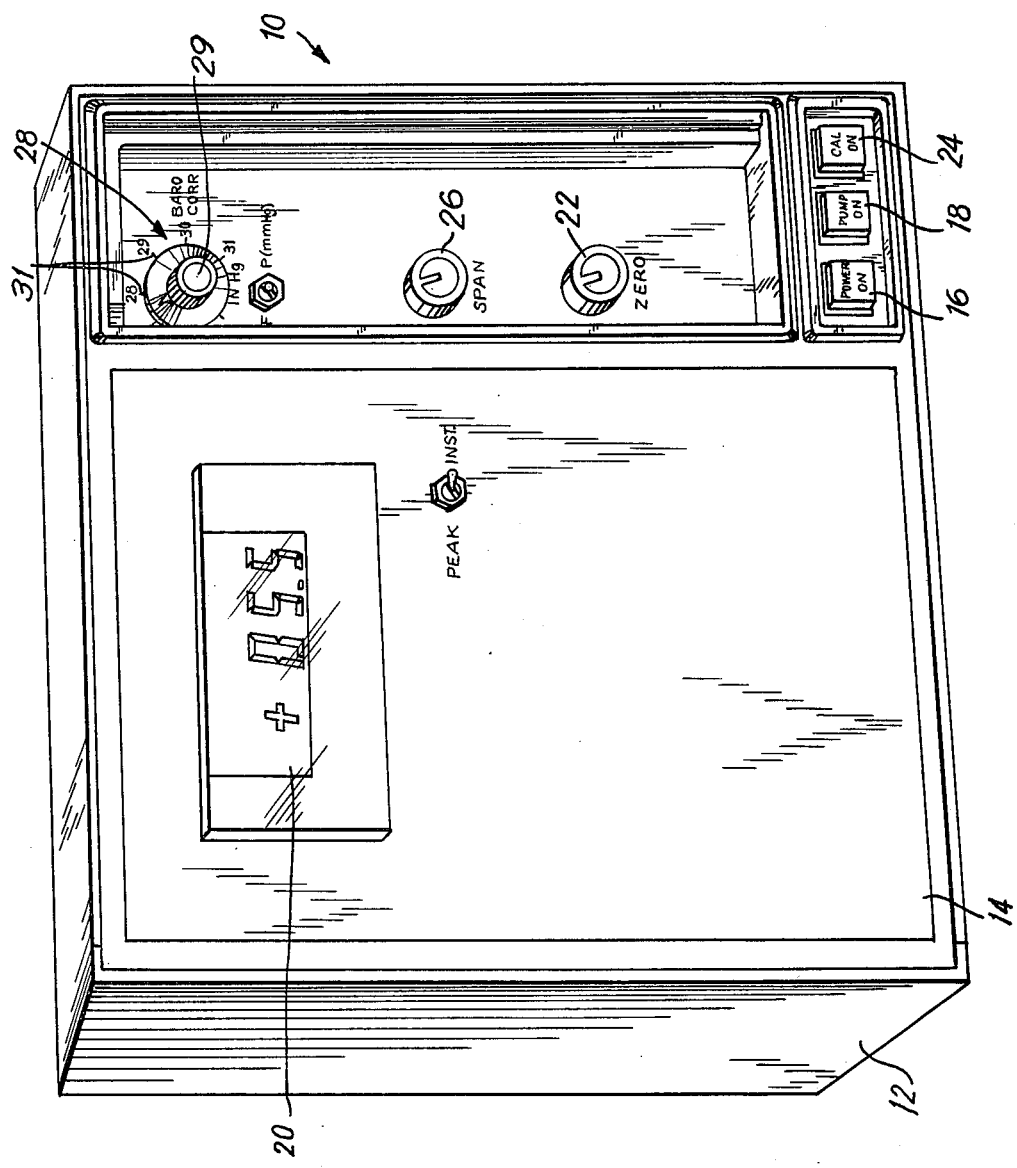
FIG. 1 is a perspective view of a gas analyzer system embodying the present invention.

The gas analyzer 10 illustrated in FIG. 1 may take various shapes and forms and contain all or part of the various features of the present invention which are hereinafter discussed in detail. The gas analyzer 10 is employed for various applications and in particular for medical applications it may be used for patient monitoring or in an operating room to detect the presence of certain gases.

The gas analyzer 10 is used with a gas pickup (not shown) that receives a sample of the gas to be analyzed and is then transmitted through the analyzer 10 in order to provide a readout on display means associated therewith. The gas analyzer 10 may include a cabinet 12 having a front panel 14 containing thereon various instrumentation necessary for the operation of the analyzer 10.

To operate the analyzer 10 the power switch 16 is activated and thereafter the pump switch 18 is energized to activate the pump (not shown) necessary to effect the flow of the sample specimen through the analyzer 10.

To check instrument calibration which may be desired occasionly, one may first allow the instrument to draw clean air at which time the analyzer 10 should read zero concentration at the display means 20. If other than zero readings appear the zero control knob 22 would be adjusted to make the display meter read zero. To check the full scale span calibration, the calibration switch 24 is depressed. This actuates the cal wedge mechanism (see FIG. 2) and appropriate scaling resistors in the display device network to effect a full scale indication of the simulated input signal. If the indication is either over or under scale the span control 26 is adjusted to show exactly full scale on the display means 20 and this restores the correct calibration to the gain circuits in the analyzer 10.

The barometric correction means 28 including knob 29 and indicating markings 31 on the front of the analyzer will be hereinafter discussed to illustrate the need to provide for the user, particularly in medical applications, a refinement in the instrumentation not previously available.

OPTICAL UNIT

Reference now to drawings in FIGS. 2-6 the optical unit 25 which is contained within the cabinet 12 of the gas analyzer 10 utilizing the infrared absorption principle for determining the quantity of one or more gases in a sample is shown. The gas analyzer optical unit 25 includes as its principal components an infrared projector means or assembly 30 and a detector means or assembly 32 in spaced axial alignment. Standing between the projector assembly 30 and detector assembly 32 is an optical assembly 34 comprised of a source end plate 36, a chamber means 38 and a detector end plate 40 all assembled together by fasteners (not shown).

A chopper disc assembly 42 is contained within a cavity 44 of plate 36 and includes a disc 43 mounted on a hub 46 affixed to shaft 48 of chopper motor 50 mounted on plate 36. A cal wedge assembly 52 is contained within a cavity 54 of plate 40 and mounted on a hub 56 affixed to shaft 58 of cal wedge motor 60 mounted on plate 40.

Figure 3:
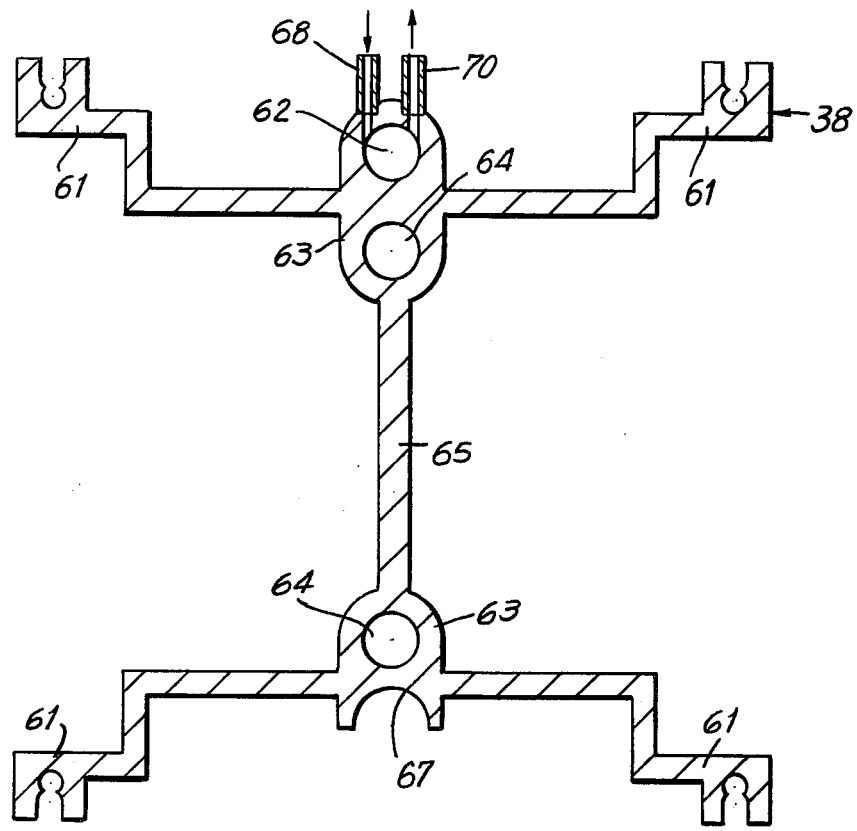
FIG. 3 is a sectional view of the sample chamber and reference chamber, taken along line 3—3 of FIG. 2.

The chamber means 38 as seen in FIG. 3 may be of the design of an extruded frame with outwardly extending mounting arm 61 such that extending axially through the head portion 63 there is provided a sample path or cavity 62 and in spaced relationship thereto is provided a reference path 64, both chambers may have cross sections of the same dimension. The diameter of the chambers may be in the range of 0.10 inch to 2.0 inches.

The reference chamber 64 and the sample chamber 62 have the same length L which may vary from 0.1 to 30 inches. Each chamber 62 and 64 is sealed at each end by windows 66 that may be epoxied in place and transparent in the spectral region of the instrument. The sample chamber 62 is provided with an inlet port 68 and an outlet port 70 to permit the sample gas to flow therethrough. The reference chamber 64 may be filled with ambient air or an inert atmosphere prior to sealing with the windows 66. The chamber means 38 may have a second head portion 63 with an interconnecting rib 65 and only a reference chamber 64 contained thereon in order to permit alternate sample tubes to be used in seat 67 and the position of the chamber means 38 reversed.

The infrared projector means 30 includes a casing 71 with an open front end 73 having an infrared emitting element or source 72 held in place by insulating bushing 74 and thermally insulated from housing assembly 34 by means of an annular gasket 76 extending between front end 73 and source end plate 36. The inside surface 78 of the infrared projector 30 has a conical shape and is highly reflective and defines cavity 80. The air space in cavity 80 defined by the interior conical surface 78 is protected from buffeting by air currents by baffle means 82. The baffle means 82 is seen to include a pair of baffle plates 84 that are disposed in seats 85 provided on the inner wall 86 of the source end plate 36 and in alignment with the sample chamber 62 and reference chamber 64. The baffle means 82 is essential to reducing to a minimum the optical noise which is generated by the infrared emitter 72.

The oblong shaped infrared emitting source 72 has essentially blackbody radiation characteristics and emits from its total surface omnidirectionally. The conical reflecting surface 78 reflects in the direction of the optical paths those beams or rays 90 and 92 which are at appropriate angular relationships with the reflecting surface 78. Beams 90 pass through the sample chamber 62 and beams 92 pass through the reference chamber 64.

The detector assembly 32 includes a housing 91 with a front open end 93 and a collecting concavely shaped mirror 94 at the rear of the housing 91 facing the front end 93. Positioned to collect and direct the beams 90 and 92 is a spectral filter 96 mounted in the housing adjacent to a detector element 93 positioned on a supporting member 100. Lead-in wires from the detector 98 are terminated on connector terminals 102. Terminals 102 are in turn connected to the preamplifier 202 at the circuit of FIG. 14.

A feature of the present invention is the provision in the detector assembly 32 of masking means 104 for back filling the interior detector cavity 106 formed within the housing 91 with selected spectrally absorbing gases. The problem in evaluating certain gases contained in the sample stream is another gas having spectral absorption lines which overlap into the region covered by the spectral filter 96 installed in the optical assembly 25 and specifically tuned to the absorption spectrum of the gas of interest. Failure to eliminate the effects of interference results in signal distortions and error in indication of true gas concentration. The need to eliminate the effect of an interferring gas is particularly needed in medical applications where certain anesthetic gases lie in spectral proximity to strongly absorbing spectra of carbon dioxide $CO_2$ which is always present in exhaled breath. An example of potential spectral overlap exists between nitrous oxide $N_2O$ and $CO_2$, and also between a number of halogenated hydrocarbons such as Penthrane, Ethrane and Halothane, and $CO_2$.

The backfill masking means 104 is obtained by making the cavity 106 leakproof. To this end the front end 93 of the housing 32 is mounted in sealed relationship to the detector end plate 40. Furthermore, a pair of spaced apart apertures 108 extend through the wall 112 of the detector end plate 40 which apertures 108 are in axial alignment with the apertures 88 and sample chamber 62 and reference chamber 64. Transparent members 110 are provided in seats 111 and in sealed relationship on the wall 112 of cavity 54 to thereby seal off chamber 106 from the environment.

Cavity filling means 114 is provided in operative relation to the chamber 106 and may include an inlet port or aperture 116 extending transversly through the wall 118 of the detector assembly housing 32. The aperture 116 communicates with the tube 120 connected to tubing 122 which terminates in an inlet valve 124. In similar fashion an exit port 126 is provided through wall 118 having a connecting tubular member 128 communicating therewith and in turn connected to a hose 130 that terminates in an outlet or vent valve 132. Having now provided for a sealed cavity 106 the instrument 24 when manufactured has the cavity or chamber 106 filed with a certain pressure, generally in the range of 1 to 25 psi and more particularly at 5 psi when the masking gas is carbon dioxide $CO_2$.

The procedure for filling the chamber 106 with gas is to apply the supply gas under pressure to inlet valve 124 which may be a spring-loaded check valve having an adjustable or fixed pressure setting. Similarly venting valve 132 can be adjustable or fixed pressure type selected for the pressure value desired inside the cavity 106. The cavity 106 is purged as the masking gas flows through the inlet valve 124 and out of the outlet valve 132. The outlet valve 132 may be calibrated to release gas from the cavity 106 at a preselected pressure to avoid rupturing of the transparent members 110. The advantage of using the detector housing cavity 106 for containing the masking gas is in the inherently long path, i.e. double pass, optical path from the entrance windows 110 to the detector element 98. The use of the cavity 106 in this fashion eliminates the need for extending the overall length of the assembly 25 or for encroaching on the total space available for the sample path L.

Figure 2:
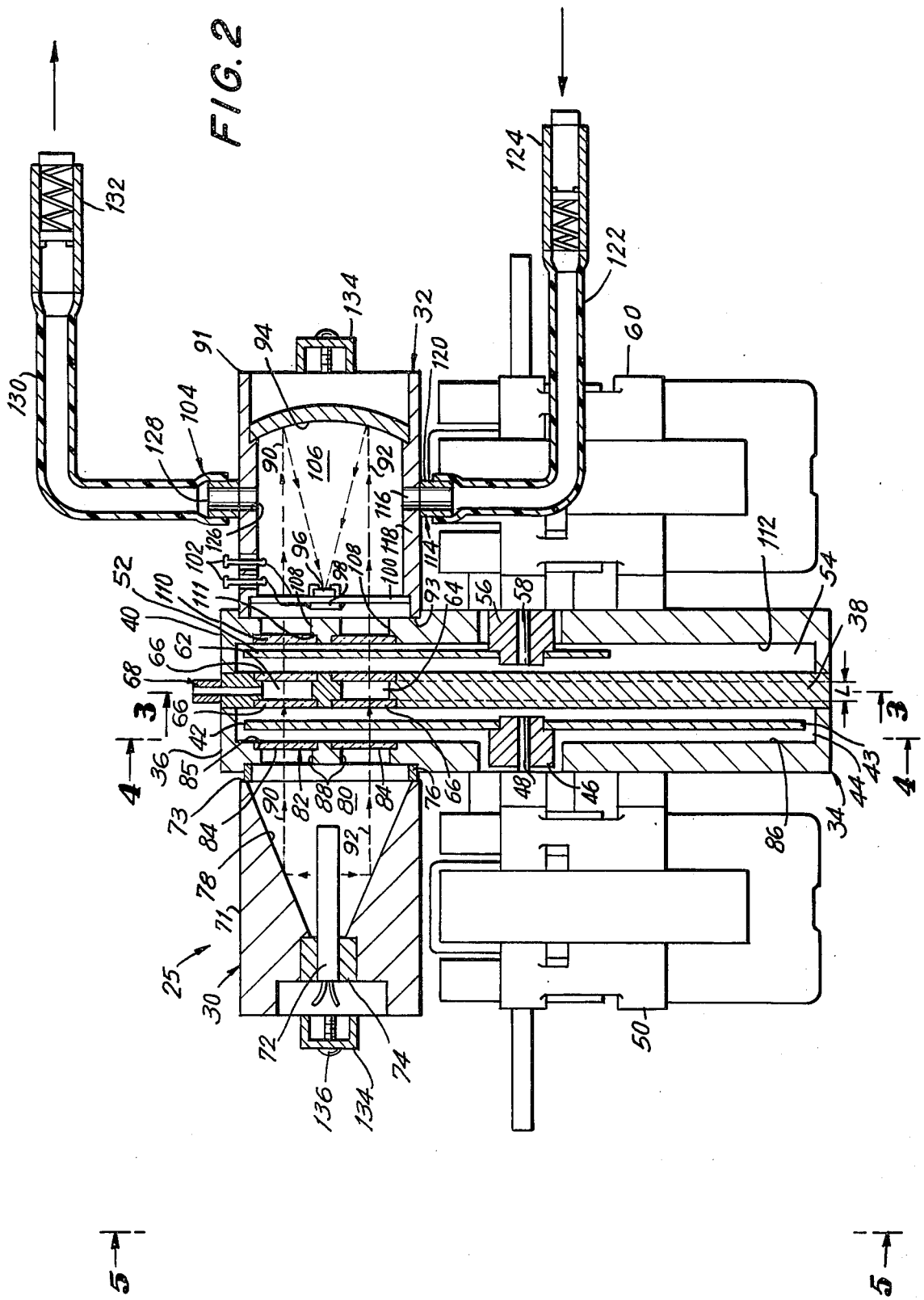
FIG. 2 is a side plan view, partially sectionalized and partially broken away, of the optical assembly portion of the gas analyzer.

Clamps 134 are provided at the end of the projector assembly 30 and detector assembly 32 to mechanically retain the projector and detector assemblies respectively as by fasteners, 136 as seen in FIG. 2 that are connected to the detector end plate 40 and source end plate 36. The photoelectric detector element 98 will vary for the particular gas under study and the emitting source 72 may be of the infrared or other bandwave spectrum.

ELECTRONIC PROCESSING SYSTEM

The electronic processing system generally identified by the numeral 200 (FIG. 14) has been provided in the present invention in order to permit amplification of the signal from the radiation detector 98 and further operation on this signal to extract the information encoded on the detector signal. The process aims to optimize the utilization of the detector generated signal to attain the highest signal to noise ratio in the output of the instrument in order to permit the maximum sensitivity in making readings of small concentrations of gases.

The waveform developed by the photoelectric detector and amplified by the electronic system is developed from the interrupted or chopped optical signal incident on the detector. The optical waveform incident on the detector is shaped by the action of the hopper disc 43 rotatingly interposed between the infrared source 30 and the detector assembly 32.

Figure 4:
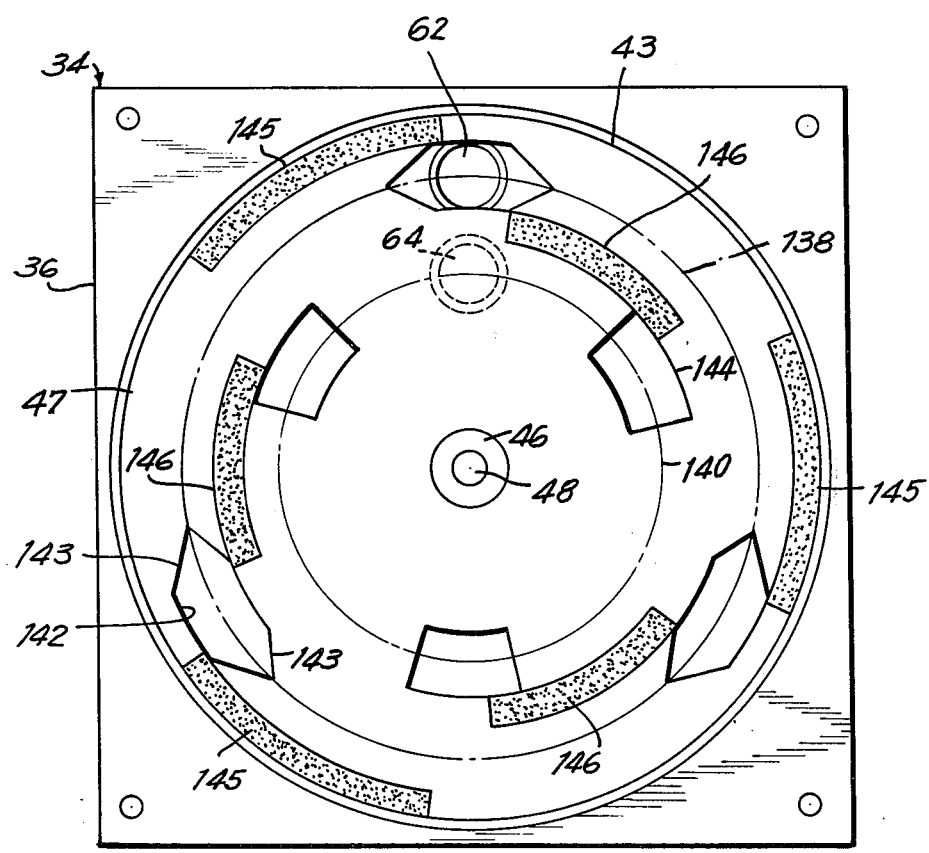
FIG. 4 is a sectional view illustrating the chopper disc, taken along lines 4—4 of FIG. 2.
Figure 5:
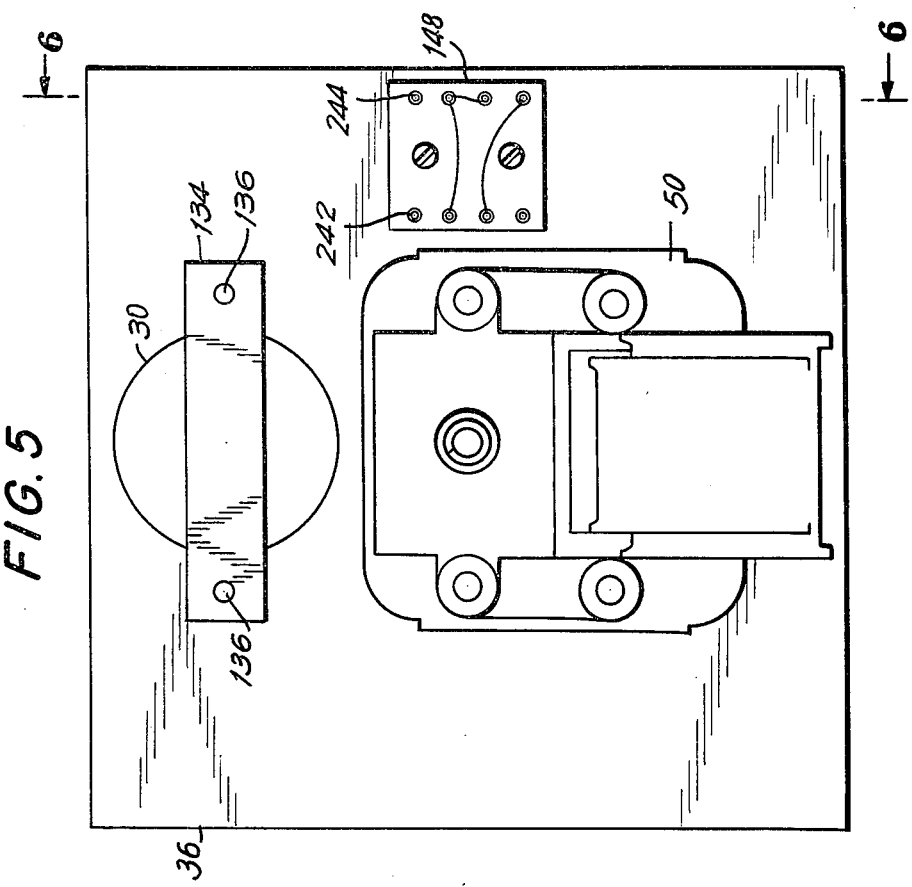
FIG. 5 is a partial end view of the optical assembly taken along lines 5—5 of FIG. 2.

FIGS. 2 and 4 show the chopper disc 43 interposed between the infrared source 30 and the infrared detector 32. Disc 43 is preferably circular shaped with a tracking surface 47 provided with an outer-track 138 and an inner-track 140. The outer-track 138, which is the signal track, is seen to include three arcuate shaped slots 142 having tapered ends 143. The inner-track 140 is seen to contain three slots 144 for use as part of the reference track.

Associated with each of the two tracks 138 and 140 is a set of timing stripes 145 and 146 associated with the respective tracks. The stripes have a reflecting finish and may be applied to the surface 46 as by painting of the chopper disc 43 which can be formed of any rigid material, such as metallic or plastic. Chopper disc 43 is affixed to the shaft 48 of the motor 50, which may be of a shaded pole design, by means of a hub 46 (FIG. 2). The chopper disc assembly 42 is preferably rotated by the motor 50, at a speed of approximately 3,300 rpm, but such speed is not critical.

Figure 6:
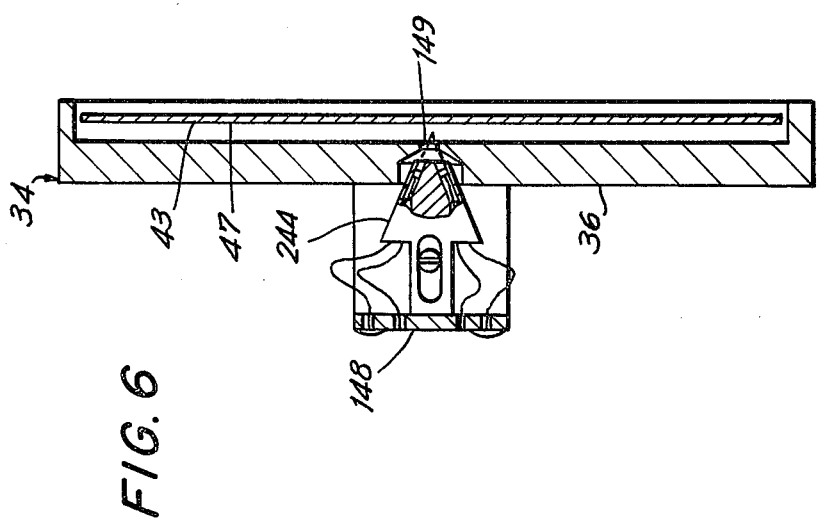
FIG. 6 is a partial sectional view illustrating the reading head positioned relative to the chopper disc, taken along lines 6—6 of FIG. 5.

In FIG. 6 it can be seen that a photoelectric head assembly 148 is provided for each track 138 and 140 on the frame 25 of the gas analyzer. Assembly 148 is in cooperative relationship with the chopper disc 43 and more particularly, with the timing stripes 145 and 146 thereon to provide output sync pulses from each track as the chopper disc 43 rotates. The reflective head assembly 148 has reflective heads 242 and 244 as illustrated in FIG. 6 disposed on the tracking side 47 of the chopper disc 43 and operates in a manner so that a sync pulse is generated each time the timing stripes 145 and 146 pass across the read head assembly 242 and 244 in a sequential relationship. An opening 149 is provided on the source end plate 36 in association with each assembly 242 and 244 to permit the light to exit therethrough and be reflected from strips 145 and 146 and be returned therethrough.

FIG. 7 shows the electrical signal developed by the detector 98 by the chopper action in the optical paths 90 and 92 and shows the reference and the sample signal lobes developed.

FIG. 8 shows the reference sync signal developed by the reference track 140 of the read head assembly 242 in relation to the detector signal, and FIG. 9 shows the sample signal developed by the sample track 138 of the read head assembly 244.

FIG. 10 shows an auxiliary synchronization signal derived from the reference sync and the sample sync waveforms which is indicated as zero sync and which is used to clamp the waveform to ground corresponding to the periods in time where the detector is completely occluded or cut-off by the chopper disc and receives no energy transmission through the sample chamber 62 of the reference chamber 64.

FIG. 11 shows the signal waveform clamped to ground during the detector dark periods so that the waveform dwells entirely in the negative polarity voltage region.

FIG. 12 shows the waveform of FIG. 7 modified by inverting the alternate half cycles corresponding to the sample pulses and combined with the direct reference pulses into a composite bipolar waveform centered at ground and having reference lobes extending in the negative voltage direction and sample lobes in the positive voltage direction. The phantom curve shown within the sample lobe shows the typical amplitude deviation resulting from gas absorption by a gas sample introduced into the sample chamber.

The resulting decrease in lobe amplitude increases the difference between voltage contribution by the reference and sample lobes and gives an upscale reading which can be calibrated in terms of gas concentration and which calibration is indicated on the readout meter 20 on the front panel of the device 10 as seen in FIG. 1.

FIG. 12 shows the effect of integrating the waveform of FIG. 11 in a filter of sufficient time constant to obtain a DC voltage value corresponding to the difference between the voltage contribution of the positive and negative excursions of the waveform of FIG. 12. This voltage is the signal that is then used to operate the output display device 20.

The user seeks information regarding gas concentration in order to make certain determinations as related to medical applications. This information is of critical importance to the health condition of a patient and/or the physician as to the level of various gases in an operating room such as $N_2O$ when used by the Anesthesiologist during operating procedures. By way of example, if the patient is an infant, then the sample specimen available on which the calculations are to be performed, may be minimal in that the volume may be as small as 0.2 cc. In order to obtain the proper readout the inventor found the teachings of the prior art did not permit the degree of reliability necessary in order to make use of samples of small volumes and to process them through a gas analyzer with the refinements that he found were necessary.

In order to provide a more refined instrument, the sampling rate must be adequately high to provide a sufficient number of samples per unit time to yield the desired overall instrument response speed. Furthermore, in the interest of maximizing detector signal to noise ratio, it is desirable to chop the infrared energy beam incident on the detector at the highest rate practically attainable. Towards this end, the chopper disc is provided with three sets of slots so at to give three complete chopping cycles per motor shaft revolution. In order to obtain a gas analyzer having the necessary refinements and precision required for the medical market, there has been provided not only three chopping cycles per revolution of disc 43 but as hereinafter discussed, with reference to FIG. 14, special efforts have been made to attain the fullest possible utilization of the detector signal by extending the measurement process applied to the waveform over 100% of its duration indicated by the distance R vs. previously generally employed durations X. The value of extending the time over which a measurement is taken derives from the effective narrowing of the noise bandwidth equivalent to the increase in signal integration time. As an illustration, consider for example, the noise signal $E_n$ generated by a resistive element of R ohms at temperature T degrees Kelvin and expressed by the equation $E_n = \sqrt{4KT\Delta FR}$; where $\Delta F$ is the noise bandwidth of measurement and $K$ is Boltzmann constant having the value $1.38 \times 10^{-23}$ Joule per degree Kelvin. By decreasing the noise bandwidth $\Delta F$ the noise voltage generated by the resistive element is proportionately decreased. The ability to provide an instrument that utilizes the full area under the sample waveform Y results in the attainment of the objective of improvement of the signal to noise ratio which in turn improves the sensitivity capability of the instrument.

In FIG. 14 the signal developed by the detector 98 is amplified by a conventional integrated circuit preamplifier stage 202 to a working signal level of approximately 1 volt. This signal is then coupled to an additional amplifier stage 204 having a capability of gain adjustment by an electronic control signal applied from external sources and comprising the automatic gain control (AGC) element of the system. The output signal of the AGC amplifier 204 is clamped to ground at appropriate points in the waveform corresponding to times defined by the zero sync pulses of FIG. 10 and effected by a conventional zero clamp circuit 206 to establish a ground reference for the processed signal to develop the relationship shown in FIG. 11.

The output signal from zero clamping circuit 206 is divided into two voltage paths; one signal path couples the signal voltage through an inverting amplifier 208 and to a conventional signal switching circuit 210, and the other path couples the signal voltage directly to another conventional signal switching circuit 212. The output from both switching circuits 210 and 212 are connected to the opposite ends of a potentiometer 214 having a center arm 216 which can be positioned to balance the effect of the signals applied at the ends thereof.

Switching circuit 210 is actuated by the sample sync waveform S of FIG. 9 and switching circuit 212 is actuated by the reference sync waveform P of FIG. 8. As a result of this circuit configuration the reference signal voltage and the sample signal voltage lobes with the sample signal lobe inverted by the action of inverting amplifier 208 appear at potentiometer arm 216 sequentially. A portion of the voltage appearing at the output terminal of switching element 212 is coupled, via line 220, to a comparator and AGC amplifier circuit 222 which compares the amplitude of the reference lobe to a preset voltage level appearing at the junction 224 of a resistor divider network formed by the serially connected resistors 226 and 228. Resistor 226 is connected to ground and resistor 228 is connected to a regulated supply voltage 230.

The output voltage signal of AGC amplifier 222 is coupled to the AGC error detector 232 which develops a control voltage that is coupled, via connection 234, to the AGC amplifier 204, in the proper amplitude and polarity as to effect amplitude stabilization of the reference pulse as shown in the composite waveform of FIG. 11 and subsequently, FIG. 12.

The signal voltage illustrated in FIG. 12 appears from the potentiometer arm 216 to ground and is coupled to the integrator circuitry 218 where the signal is integrated and filtered to yield an average value represented by a DC voltage level as shown in FIG. 14. This voltage level is then coupled, via leads 236 and 240 through scaling elements 238, which may take the form of amplifier, resistive divider networks, linearizer networks, etc., to a readout device 20 such as a conventional digital voltmeter, a chart recorder or a combination of any such or similar devices.

As shown in FIG. 14, the reference sync pickup signal voltage is provided by read head assembly 242 and is coupled to amplifier 242a yielding the output waveform P of FIG. 8. The sample read head 244 develops another sync signal voltage which is coupled to amplifier 244a yielding the sample sync signal S of FIG. 9. Sync signal voltages P and S are coupled, via leads 246 and 248, respectively, to a logic gate 250 which yields the zero sync waveform voltage of FIG. 10. This zero sync signal voltage is coupled, via lead 252, to a zero clamp circuit 206. Reference sync signal voltage P is also connected, via lead 243, to switching element 212 and sample sync voltage S is coupled, via lead 245, to switching element 210.

The circuit of FIG. 14 develops the voltage waveform of FIG. 7 at the output of detector 98 which is amplified by preamp 202. The same waveform but with the amplitude of the reference lobe stabilized to a fixed value appears at the output of automatic gain control amplifier 204. At the output of the zero clamp circuits 206 the waveform is that of FIG. 11 where the peaks of the waveform have been clamped to a zero volt reference.

The timing relationship defined by waveforms in FIGS. 8, 9, and 10, and developed by the circuits of FIG. 14 permit the integration process carried out in the integrater circuitry 218 to utilize the maximum duration of the total available detector signal by extending the integration time to approximately 100% of signal duration. This affords the maximum amount of time over which to average and smooth out the constantly but minutely varying, impulse contributions of the sample gas.

Thus, the disclosed circuitry provides a substantially constant output voltage regardless of minute input signal variations.

BAROMETRIC CORRECTION SYSTEM

The action of the gas analyzer and the measurement of absorption on which a determination of gas concentration in the sample cell depends is related to the number of gas molecules present in the optical path through the sample chamber which is a fixed dimension. Atmospheric parameters of temperature and pressure affect the number of molecules present in a given cubic space in accordance with the Charles Boyle gas law $PV = nRT$. Since the cell temperature stabilizes at a fairly constant temperature, the temperature parameter can be disregarded as a variant in this discussion. The necessity remains to compensate for atmospheric pressure changes. These changes occur as a result of weather conditions and physical location of the equipment and can be monitored on standard weather barometers. When seeking precise measurements, these changes need to be taken into account to reduce the measurement error which otherwise would occur, to acceptably low limits. To accomplish and overcome the above problem the inventor, as illustrated in FIG. 15, has provided barometric correction means 28 that may be easily and quickly set in the field, simply by operating the calibrated dial 29 contained on the front panel 14 of the unit 10.

The circuit arrangement of a preferred embodiment of a barometric correction network includes a voltage divider network consisting of a serially connected fixed resistor 276 having one end thereof connected to ground and the other end thereof connected to one end of a potentiometer 278. The other end of potentiometer 278 is adapted to be coupled to the analyzer output signal appearing on lead 236. The movable arm 280 of the potentiometer picks off a fraction of the output signal for connection to the output readout device 20. The dial calibration of the potentiometer is arranged so that at minimum potentiometer setting, the markings 31 on the front 14 corresponds to the highest barometric pressure ever expected to occur. Similarly, at the maximum potentiometer setting the marking corresponds to the lowest possible barometric pressure expected which is in the range of 25 to 31 inches of mercury. The points in between that range are proportionately distributed within that range. The user consults a standard wall barometer to determine barometric pressure of the day and sets the control knob and therefore, the arm of the potentiometer 280 to the corresponding marking on the instrument panel. This scales the signal applied to the readout device to compensate for gas expansion or compression due to the atmospheric pressure.

Accordingly, in an optical gas analyzer where the sample chamber 62 is essentially open to the atmosphere and subject to its pressure variations, the electronic means connected to the detector means for amplifying the detector signal and transforming it into an electronic signal for driving display means to measure the concentration of the sample gas passing through the sample chamber 62 relies on absorbing the radiant energy in relation to the number of the gas molecules present along the optical path of the sample chamber. The resultant readings is dependent on the ambient atmospheric pressure to which effects the sample gas is subjected such that the number of sample gas molecules present in the optical path through the sample chamber will vary in inverse proportion to the ambient atmospheric pressure.

Figure 15:
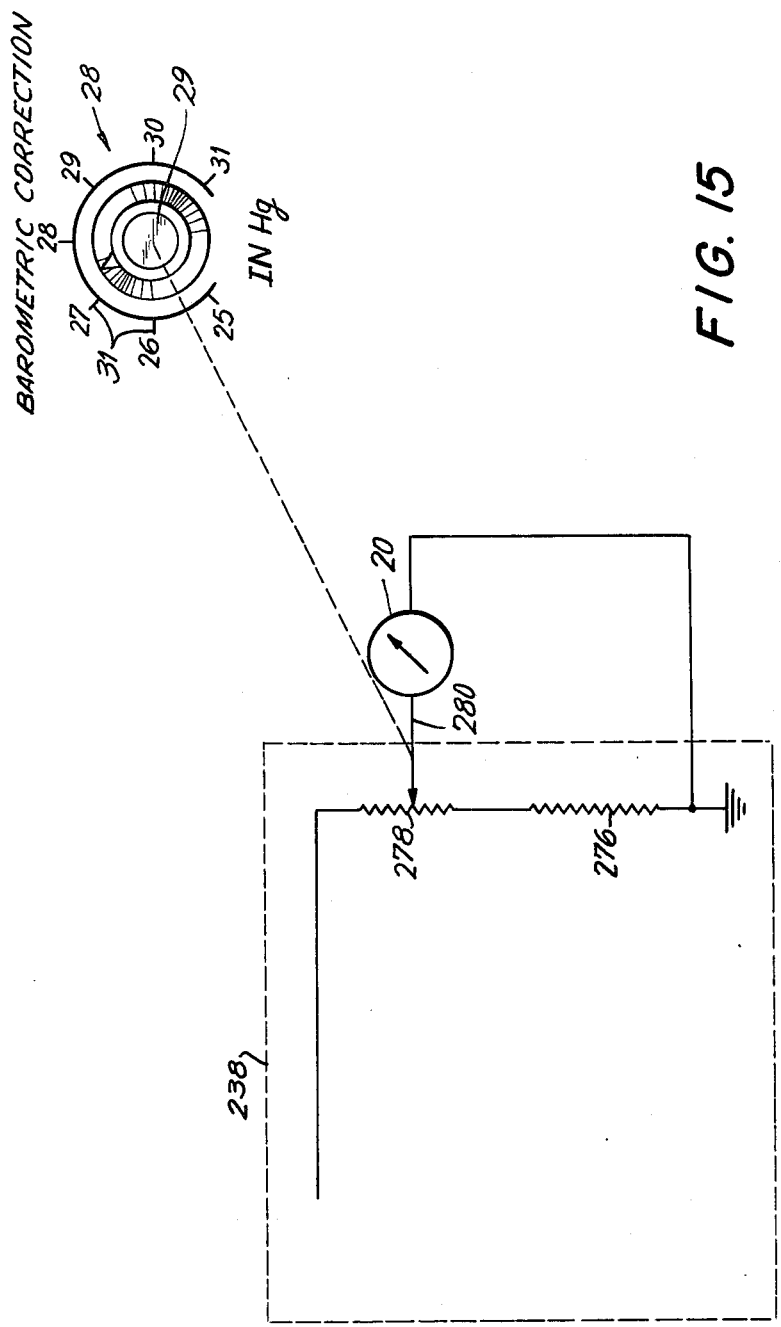
FIG. 15 is a diagram generally illustrating the circuit means of the barometric correction function as it relates to the gas analyzer.

As illustrated in FIG. 15 the attenuation means 28 connected to the electrode means 200 is so calibrated that the effect of adjusting of the attenuation means 28 is to modify the electronic signal for driving the display means 20 such that the indication shown by the display means 20 is altered to read that value which would have been indicated under conditions of standard atmospheric pressure on the same sample gas.

CONCLUSION

Although illustrative embodiments of the invention have been described in detail herein with reference to the accompanying drawings, it is to be understood that the invention is not limited to those precise embodiments, and that various changes and modifications may be effected therein without departing from the scope or spirit of the invention.

I claim:

1. In an optical gas analyzer including in combination, a sample chamber, a reference chamber, to provide dual optical paths one for analysis of a sample gas, the other for reference, radiation projector means mounted at one end of said chambers, means for chopping and directing the radiation beams alternately along the two paths, the improvement which comprises radiation detector means positioned at the other end of said chambers comprising:
   A. housing means open at the front end thereof and defining a cavity,
   B. a reflective surface within said cavity facing the front end of said housing means to reflect energy beams transmitted along said paths,
   C. a spectral filter mounted in said cavity in spaced relation to the reflective surface for receiving reflected energy beams,
   D. a detector mounted within said cavity adjacent the spectral filter to receive the radiation beams through said spectral filter,
   E. sealing means cooperating with said housing means to provide an air tight seal to said cavity and permitting energy beams to enter through the front end of said housing means to engage the reflective surface and be reflected therefrom towards the spectral filter, and
   F. masking means contained within said cavity in the form of a spectrally absorbing gas so as to eliminate the effect of an interfering gas that is contained in spectral proximity to the gas of interest in the sample gas such that the gas having spectral absorbing lines which overlap in the region covered by the spectral filter and specifically tuned to the absorption spectrum of the gas of interest is substantially eliminated.

2. In an optical gas analyzer as defined in claim 1, wherein the pressure of the spectrally absorbing gas in the cavity is in the range of 1 to 25 psi.

3. In an optical gas analyzer as defined in claim 2, wherein the pressure is approximately 5 psi.

4. In an optical gas analyzer as defined in claim 1, wherein the spectrally absorbing gas is carbon dioxide.

5. In an optical gas analyzer as defined in claim 1, wherein said masking means includes:
   a. an inlet port opening into the cavity,
   b. an inlet valve communicating with the inlet port,
   c. an outlet port opening into the cavity, and
   d. an outlet valve communicating with the outlet port, such that the cavity may be filled by having the gas enter through the inlet valve and the gas in the cavity purged through said outlet valve.

6. In an optical gas analyzer as defined in claim 1, wherein said sealing means includes
   a. a plate extending across the open end of said housing means in sealed relation thereto and having spaced apart apertures extending substantially in axial alignment with the sample and reference chambers, and
   b. a transparent member mounted in sealed relationship to each of said apertures that permits the energy beams to pass therethrough.

7. In an optical gas analyzer as defined in claim 6, wherein said outlet valve is calibrated to release gas from the cavity at a preselected pressure to avoid rupturing said transparent members.

8. In an optical gas analyzer as defined in claim 1, wherein the radiation projector means includes:
   a. casing means open at the front end thereof and defining a cavity,
   b. an infrared emitting element extending within the cavity,
   c. an interior reflective surface within the cavity to reflect beams from the emitting element through the dual optical paths of the sample and reference chambers to the detector means, and
   d. baffle means mounted in front of the infrared element to prevent buffeting by air currents so as to reduce to a minimum the optical noise which is generated by the infrared emitting element.

9. In an optical gas analyzer as defined in claim 8, wherein said baffle means includes:
   a. a plate extending across the open end of said casing means in fixed relation thereto, having spaced apart apertures extending substantially in axial alignment with the sample and reference chambers, and
   b. a transparent baffle member mounted in fixed relationship to each of said apertures that permits the energy beams to pass therethrough.

10. In an optical gas analyzer as defined in claim 9,
    a. wherein said casing means is mounted in sealed relation to the plate, and
    b. wherein the baffle members are mounted in sealed relation to the plate.

11. In an optical gas analyzer as defined in claim 10, wherein said baffle members are contained in seats on the plate.

12. In an optical gas analyzer as defined in claim 1,
    a. wherein the sample chamber is essentially open to the atmosphere and subject to its pressure variations, b. further including electronic means connected to the detector means for amplifying the detector signal and transforming it into an electronic signal for driving display means to measure the concentration of the sample gas passing through the sample chamber and absorbing the radiant energy in relation to the number of the gas molecules present along the optical path of the sample chamber, and dependent on the ambient atmospheric pressure to which effects the sample gas is subjected such that the number of sample gas molecules present in the optical path through the sample chamber will vary in inverse proportion to the ambient atmospheric pressure, and c. attenuation means connected to said electronic means and so calibrated that the effect of adjusting of the attenuation means is to modify the electronic signal for driving the display means such that the indication shown by the display means is altered to read that value which would have been indicated under conditions of standard atmospheric pressure on the same sample gas.

13. In an optical gas analyzer as defined in claim 12, wherein said attenuation means includes:
  a. an adjustable potentiometer having a dial for manually adjusting same, and
  b. a calibrated dial having markings showing the correct settings for various ambient barometric pressures for which the dial may be positioned.

14. In an optical gas analyzer as defined in claim 13, wherein said potentiometer is connected to the output of the electronic means to modify the electronic signal driving the display means to a value normalized to unity at a potentiometer calibrated setting corresponding to a selected pressure in inches of mercury, and wherein the adjustment of the potentiometer above and below said calibrated setting alters the electronic signal driving the display in a ratio appropriate to compensate the reading for changes in ambient barometric pressure.

15. In an optical gas analyzer as defined in claim 13, wherein said selected calibrated setting corresponds to 30 inches of mercury at sea level.

16. In an optical gas analyzer as defined in claim 13, wherein said calibrated setting is adjustable in the range from approximately 25 to 31 inches of mercury.

17. In an optical gas analyzer as defined in claim 13, wherein said potentiometer has an arm extending exteriorally of the gas analyzer for manual adjustment by the user.

18. In an optical gas analyzer as defined in claim 1,
  a. wherein said detector receives a first beam of energy through the sample chamber and a seconded beam of energy through the reference chamber for providing a sample signal voltage when said first beam impinges thereon and a reference signal voltage when said second beam impinges thereon;
  b. wherein the means for chopping includes interrupter means disposed in the path of said first and second infrared beams for sequentially interrupting said beams;
  c. automatic gain control means coupled to said detector for providing a constant system gain between successive signal measurements;
  d. means for developing a first sync voltage displaced in time and related to said sample signal voltage and a second sync voltage displaced in time and related to said reference signal voltage;
  e. means for combining said first and second sync voltages for providing a zero sync signal voltage;
  f. clamping means coupled to said combining means and said automatic gain control means for clamping the output signal voltage from said automatic gain control means during the high level on the zero sync signal voltage;
  g. inverting amplifier means coupled to said clamping means for providing said output signal in an inverted polarity;
  h. first and second switching means, said first switching means being coupled to said inverting amplifier and being activated by said sample signal voltage, said second switching means being coupled to said clamping means and being activated by said reference signal voltage, said first and second switching means providing a time multiplexing of said direct and inverted signal voltages;
  i. balancing means coupled to said direct and inverted signal voltages for equalizing the amplitudes of said direct and inverted signal voltages;
  j. integration means coupled to said balancing means for providing a DC voltage proportional to the amplitude of said sample signal voltage;
  k. display means coupled to said integration means for displaying said DC voltage in a suitable manner;
  l. comparator means coupled to said balancing means and a reference voltage for comparing the amplitude of said direct signal voltage with said reference voltage and providing an output voltage related to the difference therebetween; and
  m. error detector means coupled between said comparator means and said automatic gain control means for coupling the comparator means output voltage to said automatic gain control means in the proper polarity for stabalizing the gain thereof.

19. In an optical gas analyzer as defined in claim 18,
  a. wherein said comparator means includes adjustment means for setting the value of the reference voltage, and
  b. wherein said preamplifier means is coupled between said photoelectric detector and said automatic gain control means for amplifying said sample and reference signal voltages.

20. In an optical gas analyzer as defined in claim 18, wherein said display means further includes means for introducing calibrated non-linear distortions and means for digitizing said DC voltage.

21. In an optical gas analyzer as defined in claim 1,
  a. wherein the radiation means is an infrared source of energy disposed on one end of the sample chamber for emitting a first beam of infrared energy through the sample chamber, and the reference chamber is disposed proximate said infrared source of energy for receiving a second beam of infrared energy therethrough;
  b. wherein said detector is disposed to receive said first and second beam of infrared energy for providing a sample signal voltage when said first beam impinges thereon and a reference signal voltage when said second beam impinges thereon;
  c. wherein said means for chopping includes first and second infrared beams for sequentially interrupting said beams;
  d. further including means for the generation of a signal waveform at the detector, and timing wave forms by said interrupter means including a trapezoidal waveform comprised of two similar lobes per chopping cycle having flat top portions corresponding to detector dark periods, flat bottom portions corresponding to maximum irradiance in each of the two lobes, one being due to energy passing through the reference chamber, the other the sample chamber, rise and fall slopes of essentially equal durations, separate timing waveforms developed from said interrupter means and arranged to extend over each of the reference and sample lobes separately and respectively, an auxiliary zero sync waveform synthesized from the reference and sample waveforms, all in such relationship that the reference lobe extends slightly into the dark level flat top portion ahead and behind the reference lobe, and the sample sync pulse extends over the entire duration of the sample lobe and slightly into the dark level flat top portion ahead and behind the sample lobe, and the zero sync pulse synthesized from the two exists within the time gaps between the two and consequently over periods of slightly less than the dark level durations manifested by the corresponding flat tops of the detector signal waveform, this arrangement being specifically valuable and necessary for providing adequate tolerances in mechanical relationship and electronic timing to make further adjustments uncritical, e. means for electronically processing the detector signal in conjunction with the reference, sample, and zero sync signals, and f. readout means in circuit relationship to the signal attenuation through the sample chamber to the unattenuated value when sample gas is not present, and calibrate the same to read the concentration of gas specific to the wave length of the detector with its associated filter proportional to the signal difference between the value corresponding to no attenuation without sample gas and the value with the sample gas filling the sample cell, thereby enabling the gas analyzer to read out the concentration of the sample gas.

22. In an optical gas analyzer including in combination, a sample chamber, a reference chamber, to provide dual optical paths one for analysis of a sample gas, the other for reference, radiation projector means mounted at one end of said chambers, means for chopping and directing the radiation beams alternately along the two paths, the improvement which comprises radiation detector means positioned at the other end of said chambers comprising:

A. housing means open at the front end thereof and defining a cavity,

B. a reflective surface within said cavity facing the front end of said housing means to reflect energy beams transmitted along said paths, C. a spectral filter mounted in said cavity in spaced relation to the reflective surface for receiving reflected energy beams, D. detector means mounted within said cavity adjacent the spectral filter, E. sealing means cooperating with said housing means to provide an air tight seal to said cavity and permitting energy beams to enter through the front end of said housing means to engage the reflective surface and be reflected therefrom towards the spectral filter, wherein said sealing means includes:

1. a plate extending across the open end of said housing means in sealed relation thereto and having spaced apart apertures extending substantially in axial alignment with the sample and reference chambers, and 2. a transparent member mounted in sealed relationship to each of said apertures that permits the energy beams to pass therethrough, and F. masking means contained within said cavity in the form of a spectrally absorbing gas so as to eliminate the effect of an interfering gas that is contained in spectral proximity to the gas of interest in the sample gas such that the gas having spectral absorbing lines which overlap in the region covered by the spectral filter and specifically tuned to the absorption spectrum of the gas of interest is substantially eliminated, wherein said masking means includes:

1. an inlet port opening into the cavity, 2. an inlet valve communicating with the inlet port, 3. an outlet port opening into the cavity, and 4. an outlet valve communicating with the outlet port, such that the cavity may be filled by having the gas enter through the inlet valve and the gas in the cavity purged through said outlet valve.

23. In an optical gas analyzer as defined in claim 22, wherein the radiation projector means includes:

a. casing means open at the front end thereof and defining a cavity, b. an infrared emitting element extending within the cavity, c. an interior reflective surface within the cavity to reflect beams from the emitting element through the dual optical paths of the sample and reference chambers to the detector means, and d. baffle means mounted in front of the infrared element to prevent buffeting by air currents so as to reduce to a minimum the optical noise which is generated by the infrared emitting element, wherein said baffle means includes:

1. a plate extending across the open end of said casing means in fixed relation thereto, having spaced apart apertures extending substantially in axial alignment with the sample and reference chambers, and 2. a transparent baffle member mounted in fixed relationship to each of said apertures that permits the energy beams to pass therethrough.

24. In an optical analyzer as defined in claim 22, a. wherein the sample chamber is essentially open to the atmosphere and subject to its pressure variations, b. further including electronic means connected to the detector means for amplifying the detector signal and transforming it into an electronic signal for driving display means to measure the concentration of the sample gas passing through the sample chamber and absorbing the radiant energy in relation to the number of the gas molecules present along the optical path of the sample chamber, and dependent on the ambient atmospheric pressure to which effects the sample gas is subjected such that the number of sample gas molecules present in the optical path through the sample chamber will vary in inverse proportion to the ambient atmospheric pressure, and c. attenuation means connected to said electronic means and so calibrated that the effect of adjusting of the attenuation means is to modify the electronic signal for driving the display means such that the indication shown by the display means is altered to read that value which would have been indicated under conditions of standard atmospheric pressure on the same sample gas.

25. In an optical gas analyzer including in combination, a sample chamber, a reference chamber to provide dual optical paths one for analysis of a sample gas, the other for reference, means for alternately chopping the two paths, detector means positioned at one end of the dual optical paths, the improvement which comprises radiation projector means positioned at the other end of the dual optical paths comprising:
   A. casing means open at the front end thereof and defining a cavity,
   B. an infrared emitting element extending within the cavity,
   C. an interior reflective surface within the cavity to reflect means from the emitting element through the dual optical paths of the sample and reference chambers to the detector means,
   D. a plate extending across the open end of said casing means in fixed relation thereto, having spaced apart apertures extending substantially in axial alignment with the sample and reference chambers,
   E. means for mounting said plate in sealed relation to said front end of said casing means,
   F. baffle means mounted on said plate in front of the infrared element to prevent buffeting by air currents so as to reduce to a minimum the optical noise which is generated by the infrared emitting element, and
   G. said baffle means comprises a transparent baffle member mounted in fixed sealed relationship to each one of said apertures such that each said baffle member permits the energy beams to pass therethrough.

26. In an optical gas analyzer as defined in claim 25, wherein said baffle members are contained in seats on the plate.

27. In an optical gas analyzer as defined in claim 25,
   a. wherein the infrared emitting element disposed on one end of the sample chamber emits a first beam of infrared energy through the sample chamber, and a second beam of energy through the reference chamber;
   b. wherein the detector means is disposed to receive said first and second beam of energy for providing a sample signal voltage when said first beam impinges thereon and a reference signal voltage when said second beam impinges thereon;
   c. wherein the chopping means includes interrupter means disposed in the path of said first and second infrared beams for sequentially interrupting said beams;
   d. automatic gain control means coupled to said detector means for providing a constant system gain between successive signal measurements;
   e. means for developing a first sync voltage displaced in time and related to said sample signal voltage and a second sync voltage displaced in time and related to said reference signal voltage;
   f. means for combining said first and second sync voltages for providing a zero sync signal voltage;
   g. clamping means coupled to said combining means and said automatic gain control means for clamping the output signal voltage from said automatic gain control means during the high level on the zero sync signal voltage;
   h. inverting amplifier means coupled to said clamping means for providing said output signal voltage in an inverted polarity;
   i. first and second switching means, said first switching means being coupled to said inverting amplifier and being activated by said sample signal voltage, said second switching means being coupled to said clamping means and being activated by said reference signal voltage, said first and second switching means providing a time multiplexing of said direct and inverted signal voltages;
   j. balancing means coupled to said direct and inverted signal voltages;
   k. integration means coupled to said balancing means for providing a DC voltage proportional to the amplitude of said simple signal voltage;
   l. display means coupled to said integration means for displaying said DC voltage in a suitable manner;
   m. comparator means coupled to said balancing means and a reference voltage for comparing the amplitude of said direct signal voltage with said reference voltage and providing an output voltage related to the difference therebetween; and
   n. error detector means coupled between said comparator means and said automatic gain control means for coupling the comparator means output voltage to said automatic gain control means in the proper polarity for stabilizing the gain thereof.

28. In an optical gas analyzer as defined in claim 27, wherein said comparator means includes adjustment means for setting the value of the reference voltage.

29. In an optical gas analyzer as defined in claim 27, wherein said preamplifier means is coupled between said first photoelectric detector and said automatic gain control means for amplifying said sample and reference signal voltages.

30. In an optical gas analyzer as defined in claim 27, wherein said display means further includes means for introducing calibrated non-linear distortions and means for digitizing said DC voltage.

31. An optical gas analyzer for determining the concentration of a gas in a sample chamber, comprising:
   A. an infrared source of energy disposed on one end of said sample chamber for emitting a first beam of infrared energy through said sample chamber;
   B. a reference chamber disposed proximate said infrared source of energy for receiving a second beam of infrared energy therethrough;
   C. a first photoelectric detector disposed to receive said first and second beam of infrared energy for providing a sample signal voltage when said first beam impinges thereon and a reference signal voltage when said second beam impinges thereon;
   D. interrupter means disposed in the path of said first and second infrared beams for sequentially interrupting said beams;
   E. automatic gain control means coupled to said first detector for providing a constant system gain between successive signal measurements;
   F. means for developing a first sync voltage displaced in time and related to said sample signal voltage and a second sync voltage displaced in time and related to said reference signal voltage;
   G. means for combining said first and second sync voltages for providing a zero sync signal voltages;

H. clamping means coupled to said combining means and said automatic gain control means for clamping the output signal voltage from said automatic gain control means during the high level on the zero sync signal voltage;

I. inverting amplifier means coupled to said clamping means for providing said output signal voltage in an inverted polarity;

J. first and second switching means, said first switching means being coupled to said inverting amplifier and being activated by said sample signal voltage, said second switching means being coupled to said clamping means and being activated by said reference signal voltage, said first and second switching means providing a time multiplexing of said direct and inverted signal voltages;

K. balancing means coupled to said direct and inverted signal voltages for equalizing the amplitudes of said direct and inverted signal voltages;

L. integration means coupled to said balancing means for providing a DC voltage proportional to the amplitude of said sample signal voltage;

M. display means coupled to said interruption means for displaying said DC voltages in a suitable manner;

N. comparator means coupled to said balancing means and a reference voltage for comparing the amplitude of said direct signal voltage with said reference voltage and providing an output voltage related to the difference therebetween; and O. error detector means coupled between said comparator means and said automatic gain control means for coupling the comparator means output voltage to said automatic gain control means in the proper polarity for stabalizing the gain thereof.

32. An optical gas analyzer as defined in claim 31, wherein said interrupter means includes a chopper disc having circumferentially displaced apertures therein, said apertures being adapted to sequentially interrupt said infrared beams as said disc is journaled about its axis.

33. An optical gas analyzer as defined in claim 32, wherein said chopper disc further includes reflective stripes.

34. An optical gas analyzer as defined in claim 33, further including a second and third light source and a second and third detector, said light sources and said detectors being disposed to cooperate with said reflective stripes to provide said first and second sync voltage.

35. An optical gas analyzer as defined in claim 34, wherein three sets of apertures and three sets of stripes are provided on said chopper disc.

36. An optical gas analyzer as defined in claim 31, wherein said display means further includes means for introducing calibrated non-linear distortions and means for digitizing said DC voltage.

37. An optical gas analyzer as defined in claim 31, and further including:
a. housing means open at the front end thereof and defining a cavity,
b. a reflective surface within said cavity facing the front end of said housing means to reflect the first and second beams of energy,
c. a spectral filter mounted in said cavity in spaced relation to the reflective surface for receiving reflected energy beams.

d. said detector mounted within said cavity adjacent the spectral filter,
e. sealing means cooperating with said housing means to provide an air tight seal to said cavity and permitting the energy beams to enter through the front end of said housing means to engage the reflective surface and be reflected therefrom towards the spectral filter, and
f. masking means contained within said cavity in the form of a spectrally absorbing gas so as to eliminate the effect of an interfering gas that is contained in spectral proximity to the gas of interest in the sample gas such that the gas having spectral absorbing lines which overlap in the region covered by the spectral filter and specifically tuned to the absorption spectrum of the gas of interest is substantially eliminated.

38. An optical gas analyzer as defined in claim 37, wherein said masking means includes:
a. an inlet port opening into the cavity,
b. an inlet valve communicating with the inlet port,
c. an outlet port opening into the cavity, and
d. an outlet valve communicating with the outlet port, such that the cavity may be filled by having the gas enter through the inlet valve and the gas in the cavity purged through said outlet valve.

39. An optical gas analyzer as defined in claim 37, wherein said sealing means includes:
a. a plate extending across the open end of said housing means in sealed relation thereto and having spaced apart apertures extending substantially in axial alignment with the sample and reference chambers, and
b. a transparent member mounted in sealed relationship to each of said apertures that permits the energy beams to pass therethrough.

40. An optical gas analyzer as defined in claim 31, and further including:
a. casing means open at the front end thereof and defining a cavity,
b. said infrared source extending within the cavity,
c. an interior reflective surface within the cavity to reflect means from the emitting element through the sample and reference chambers to the detector, and
d. baffle means mounted in front of the infrared source to prevent buffeting by air currents so as to reduce to a minimum the optical noise which is generated by the infrared source.

41. An optical gas analyzer as defined in claim 40, wherein said baffle means includes:
a. a plate extending across the open end of said casing means in fixed relation thereto, having spaced apart apertures extending substantially in axial alignment with the sample and reference chambers, and
b. a transparent baffle member mounted in fixed relationship to each of said apertures that permits the energy beams to pass therethrough.

42. The method of obtaining a DC output voltage related to the amount of concentration of a gas in a sample chamber comprising the steps of:
A. providing a source of infrared energy disposed on one end of said sample chamber, said energy source emitting a first beam of energy through said chamber;
B. providing a reference chamber disposed proximate said source of energy for receiving a second beam of infrared energy therethrough;

C. providing a sample signal voltage and a reference signal voltage when said first and second beam respectively impinges upon a first photoelectric detector;

D. interrupting said first and second infrared beam in a sequential manner;

E. stabilizing the gain between successive signal measurement of the first detector output voltage by automatic gain control circuit means;

F. developing a first sync voltage displaced in time and related to said sample signal voltage and a second sync voltage displaced in time and related to said reference signal voltage;

G. combining said first and second sync voltages to provide a zero sync signal voltage;

H. clamping the output signal voltage from said automatic gain control circuit means during the high level on the zero sync signal voltage;

I. inverting said output signal voltage;

J. providing a time multiplexing of said direct and inverted signal voltages;

K. equalizing the amplitudes of said direct and inverted signal voltages;

L. integrating said sample signal voltage to provide a DC voltage proportional to the amplitude of said signal voltage;

M. displaying said DC voltage;

N. comparing the amplitude of said direct signal voltage with said reference voltage to provide an output voltage related to the difference therebetween; and O. coupling said difference voltage to said automatic gain control means in the proper polarity for stabilizing the gain thereof.

43. The method as defined in claim 42, and further including the step of baffling said source of infrared energy to prevent buffeting by air currents, whereby the optical noise is reduced to a minimum.

44. The method as defined in claim 43, wherein said step of baffling includes:

a. providing a plate extending across the source of infrared energy, and b. selecting said plate so that the beams of energy can pass therethrough.

* * * * *